(12) United States Patent
Rimbaugh et al.

(10) Patent No.: US 6,592,594 B2
(45) Date of Patent: Jul. 15, 2003

(54) BRONCHIAL OBSTRUCTION DEVICE DEPLOYMENT SYSTEM AND METHOD

(75) Inventors: Jenni Rimbaugh, Bothell, WA (US); Lauri J. DeVore, Seattle, WA (US)

(73) Assignee: Spiration, Inc., Redmond, WA (US)

( * ) Notice: Subject to any disclaimer, the term of this patent is extended or adjusted under 35 U.S.C. 154(b) by 0 days.

(21) Appl. No.: 10/052,875

(22) Filed: Oct. 25, 2001

(65) Prior Publication Data

US 2003/0083671 A1 May 1, 2003

(51) Int. Cl.$^7$ .............................................. A61B 17/12
(52) U.S. Cl. ....................................................... 606/108
(58) Field of Search ................................ 606/108, 200, 606/198, 191

(56) References Cited

U.S. PATENT DOCUMENTS

| | | | |
|---|---|---|---|
| 3,760,808 A | * 9/1973 | Bleuer | |
| 4,681,110 A | * 7/1987 | Wiktor | |
| 5,158,548 A | * 10/1992 | Lau et al. | |
| 5,453,090 A | * 9/1995 | Martinez et al. | |
| 5,603,698 A | * 2/1997 | Roberts et al. | 604/104 |
| 6,149,664 A | * 11/2000 | Kurz | 606/194 |
| 6,165,179 A | * 12/2000 | Cathcart et al. | 606/108 |
| 6,174,323 B1 | * 1/2001 | Biggs et al. | 606/232 |
| 6,258,100 B1 | * 7/2001 | Alferness et al. | 606/108 |
| 6,293,951 B1 | * 9/2001 | Alferness et al. | 606/108 |
| 6,328,689 B1 | * 12/2001 | Gonzalez et al. | 600/37 |
| 6,491,706 B1 | * 12/2002 | Alferness et al. | 606/157 |

FOREIGN PATENT DOCUMENTS

GB  2 324 729 A  * 11/1998

* cited by examiner

*Primary Examiner*—Ralph A. Lewis
(74) *Attorney, Agent, or Firm*—Graybeal Jackson Haley LLP

(57) ABSTRACT

A system and method deploys a bronchial obstruction device in an air passageway communicating with a lung portion to be at least temporarily collapsed. The system includes a conduit configured to be passed down a trachea, into a bronchus communicating with the trachea and into the air passageway communicating with the lung portion. The system further includes a capsule dimensioned to house the bronchial obstruction device and to be advanced down an internal lumen of the conduit into the air passageway. The capsule has a break-away distal end configured to release the bronchial obstruction device for deployment in the air passageway upon being pushed from the capsule by a pusher member.

34 Claims, 3 Drawing Sheets

BRONCHIAL OBSTRUCTION DEVICE DEPLOYMENT SYSTEM AND METHOD

BACKGROUND OF THE INVENTION

The present invention is generally directed to a treatment of Chronic Obstructive Pulmonary Disease (COPD). The present invention is more particularly directed to bronchial obstruction device deployment systems and methods.

Chronic Obstructive Pulmonary Disease (COPD) has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia, and smooth muscle hypertrophy in terminal bronchioles.

The incidence, prevalence, and health-related costs of COPD are on the rise. Mortality due to COPD is also on the rise. In 1991 COPD was the fourth leading cause of death in the United States and had increased 33% since 1979.

COPD affects the patient's whole life. It has three main symptoms: cough; breathlessness; and wheeze. At first, breathlessness may be noticed when running for a bus, digging in the garden, or walking up hill. Later, it may be noticed when simply walking in the kitchen. Over time, it may occur with less and less effort until it is present all of the time.

COPD is a progressive disease and currently has no cure. Current treatments for COPD include the prevention of further respiratory damage, pharmacotherapy, and surgery. Each is discussed below.

The prevention of further respiratory damage entails the adoption of a healthy lifestyle. Smoking cessation is believed to be the single most important therapeutic intervention. However, regular exercise and weight control are also important. Patients whose symptoms restrict their daily activities or who otherwise have an impaired quality of life may require a pulmonary rehabilitation program including ventilatory muscle training and breathing retraining. Long-term oxygen therapy may also become necessary.

Pharmacotherapy may include bronchodilator therapy to open up the airways as much as possible or inhaled β-agonists. For those patients who respond poorly to the foregoing or who have persistent symptoms, Ipratropium bromide may be indicated. Further, courses of steroids, such as corticosteroids, may be required. Lastly, antibiotics may be required to prevent infections and influenza and pheumococcal vaccines may be routinely administered. Unfortunately, there is no evidence that early, regular use of pharmacotherapy will alter the progression of COPD.

About 40 years ago, it was first postulated that the tethering force that tends to keep the intrathoracic airways open was lost in emphysema and that by surgically removing the most affected parts of the lungs, the force could be partially restored. Although the surgery was deemed promising, the procedure was abandoned.

The lung volume reduction surgery (LVRS) was later revived. In the early 1990's, hundreds of patients underwent the procedure. However, the procedure has fallen out of favor due to the fact that Medicare stopping reimbursing for LVRS. Unfortunately, data is relatively scarce and many factors conspire to make what data exists difficult to interpret. The procedure is currently under review in a controlled clinical trial. What data does exist tends to indicate that patients benefited from the procedure in terms of an increase in forced expiratory volume, a decrease in total lung capacity, and a significant improvement in lung function, dyspnea, and quality of life. However, the surgery is not without potential complications. Lung tissue is very thin and fragile. Hence, it is difficult to suture after sectioning. This gives rise to potential infection and air leaks. In fact, nearly thirty percent (30%) of such surgeries result in air leaks.

Improvements in pulmonary function after LVRS have been attributed to at least four possible mechanisms. These include enhanced elastic recoil, correction of ventilation/perfusion mismatch, improved efficiency of respiratory muscaulature, and improved right ventricular filling.

Lastly, lung transplantation is also an option. Today, COPD is the most common diagnosis for which lung transplantation is considered. Unfortunately, this consideration is given for only those with advanced COPD. Given the limited availability of donor organs, lung transplant is far from being available to all patients.

In view of the need in the art for new and improved therapies for COPD which provide more permanent results than pharmacotherapy while being less invasive and traumatic than LVRS, at least two new therapies have recently been proposed. Both of these new therapies provide lung size reduction by permanently or temporarily collapsing at least a portion of a lung.

In accordance with a first one of these therapies, and as described in U.S. Pat. No. 6,258,100 assigned to the assignee of the present invention and incorporated herein by reference, a lung may be collapsed by obstructing an air passageway communicating with the lung portion to be collapsed. The air passageway may be obstructed by placing a bronchial obstruction device in the air passageway. The bronchial obstruction device may be a plug-like device which precludes air flow in both directions or a one-way valve which permits air to be exhaled from the lung portion to be collapsed while precluding air from being inhaled into the lung portion. Once the air passageway is sealed, the residual air within the lung will be absorbed over time to cause the lung portion to collapse.

As further described in U.S. Pat. No. 6,258,100, the lung portion may be collapsed by inserting a conduit into the air passageway communicating with the lung portion to be collapsed. An obstruction device, such as a one-way valve is then advanced down the conduit into the air passageway. The obstruction device is then deployed in the air passageway for sealing the air passageway and causing the lung portion to be collapsed.

The second therapy is fully described in copending U.S. application Ser. No. 09/534,244, filed Mar. 23, 2000, for LUNG CONSTRICTION APPARATUS AND METHOD and, is also assigned to the assignee of the present invention. As described therein, a lung constriction device including a sleeve of elastic material is configured to cover at least a portion of a lung. The sleeve has a pair of opened ends to permit the lung portion to be drawn into the sleeve. Once drawn therein, the lung portion is constricted by the sleeve to reduce the size of the lung portion.

Both therapies hold great promise for treating COPD. Neither therapy requires sectioning and suturing of lung tissue.

While either therapy alone would be effective in providing lung size reduction and treatment of COPD, it has recently been proposed that the therapies may be combined for more effective treatment. More specifically, it has been proposed that the therapies could be administered in series, with the first mentioned therapy first applied acutely for evaluation of the effectiveness of lung size reduction in a patient and which lung portions should be reduced in size to obtain the best results. The first therapy is ideal for this as it is noninvasive and could be administered in a physician's office. Once the effectiveness of lung size reduction is confirmed and the identity of the lung portions to be collapsed is determined, the more invasive second mentioned therapy may be administered.

In order to employ the first mentioned therapy described in U.S. Pat. No. 6,258,100, it is necessary to deploy the bronchial obstruction device within an air passageway. The deployment must be reliable in that it must be done in a well controlled manner to assure placement in the proper location. It must also be done in a sterile manner. Patients suffering from COPD generally have compromised health. Sterile deployment may therefore prevent a catastrophic infection from occurring in those patients who are in a weakened state. The present invention addresses these issues by providing bronchial obstruction device deployment systems and method which provide more reliable device placement and sterile deployment conditions.

SUMMARY OF THE INVENTION

The present invention provides a system for deploying a bronchial obstruction device in an air passageway communicating with a lung portion to be at least temporarily collapsed by the bronchial obstruction device. The system includes a conduit having an internal lumen and configured to be passed down a trachea, into a bronchus communicating with the trachea and into the air passageway communicating with the lung portion, and a capsule dimensioned to house the bronchial obstruction device and to be advanced down the internal lumen into the air passageway. The capsule is configured to release the bronchial obstruction device for deployment in the air passageway.

Preferably, the capsule sealingly houses the bronchial obstruction device. The capsule may further include a breakaway end portion to release the bronchial obstruction device.

The system may further include a pusher that pushes the bronchial obstruction device from the capsule. The capsule may further include an elongated extension communicating with the capsule and dimensioned for receiving the pusher. The elongated extension may be separated from the capsule by a break-away wall.

The capsule may be formed of flexible material for collapsing within the internal lumen or maybe formed of a rigid material. The capsule includes a distal end which may be configured to release the bronchial obstruction device. The distal end of the capsule may further have a rounded shape.

The invention still further provides a system for deploying a bronchial obstruction device in an air passageway communicating with a lung portion to be at least temporarily collapsed by the bronchial obstruction device. The system includes lumen means for being passed down a trachea, into a bronchus communicating with the trachea and into the air passageway communicating with the lung portion, and deployment means for housing the bronchial obstruction device and dimensioned for advancement down the lumen means into the air passageway, the deployment means having a distal end for releasing the bronchial obstruction device within the air passageway.

The invention still further provides a method of deploying a bronchial obstruction device in an air passageway communicating with a lung portion to be at least temporarily collapsed. The method includes the steps of placing the bronchial obstruction device in a housing, guiding a conduit having an internal lumen down a trachea, into a bronchus communicating with the trachea and into the air passageway communicating with the lung portion, advancing the housing down the internal lumen of the conduit into the air passageway, and releasing the bronchial obstruction device from the housing to deploy the bronchial obstruction device in the air passageway.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify identical elements, and wherein:

DETAILED DESCRIPTION OF THE PREFERRED EMBODIMENTS

Figure 1:
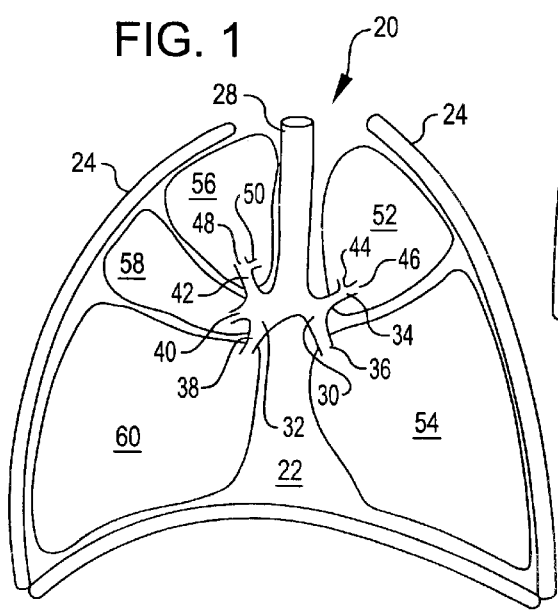
FIG. 1 is a simplified sectional view of a thorax illustrating a healthy respiratory system.

Referring now to FIG. 1, it is a sectional view of a healthy respiratory system. The respiratory system 20 resides within the thorax 22 which occupies a space defined by the chest wall 24 and the diaphragm 26.

The respiratory system 20 includes the trachea 28, the left mainstem bronchus 30, the right mainstem bronchus 32, the bronchial branches 34, 36, 38, 40, and 42 and sub-branches 44, 46, 48, and 50. The respiratory system 20 further includes left lung lobes 52 and 54 and right lung lobes 56, 58, and 60. Each bronchial branch and sub-branch communicates with a respective different portion of a lung lobe, either the entire lung lobe or a portion thereof. As used herein, the term "air passageway" is meant to denote either a bronchial branch or sub-branch which communicates with a corresponding individual lung lobe or lung lobe portion to provide inhaled air thereto or conduct exhaled air therefrom.

Characteristic of a healthy respiratory system is the arched or inwardly arcuate diaphragm 26. As the individual inhales, the diaphragm 26 straightens to increase the volume of the thorax 22. This causes a negative pressure within the thorax. The negative pressure within the thorax in turn causes the lung lobes to fill with air. When the individual exhales, the diaphragm returns to its original arched condition to decrease the volume of the thorax. The decreased volume of the thorax causes a positive pressure within the thorax which in turn causes exhalation of the lung lobes.

Figure 2:
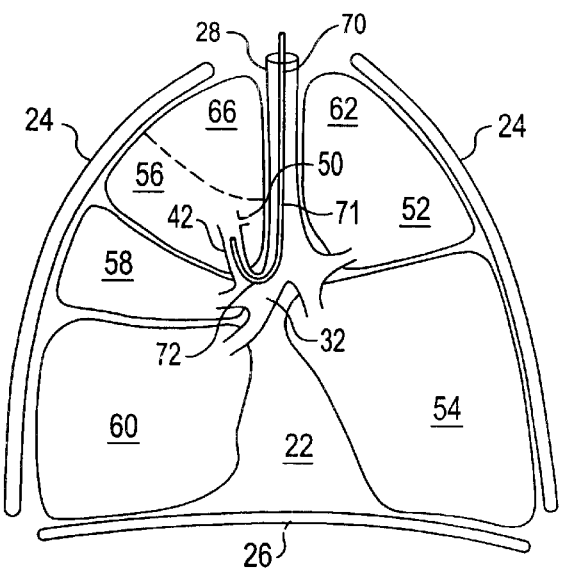
FIG. 2 is a sectional view similar to FIG. 1 but illustrating a respiratory system suffering from COPD and the execution of a first step in treating the COPD condition in accordance with the present invention.

In contrast to the healthy respiratory system of FIG. 1, FIG. 2 illustrates a respiratory system suffering from COPD. Here it may be seen that the lung lobes 52, 54, 56, 58, and 60 are enlarged and that the diaphragm 26 is not arched but substantially straight. Hence, this individual is incapable of breathing normally by moving the diaphragm 28. Instead, in order to create the negative pressure in the thorax 22 required for breathing, this individual must move the chest wall outwardly to increase the volume of the thorax. This results in inefficient breathing causing these individuals to breathe rapidly with shallow breaths. It has been found that the apex portion 62 and 66 of the upper lung lobes 52 and 56, respectively, are most affected by COPD.

In accordance with the present invention, COPD treatment or evaluation is initiated by feeding a conduit 70 down the trachea 28, into a mainstream bronchus such as the right mainstem bronchus 32, and into an air passageway such as the bronchial branch 42 or the bronchial sub-branch 50. The conduit 70 may be a catheter or a bronchoscope as are well known in the art. A bronchial obstruction device, contained within a housing, is then advanced down an internal lumen 71 of the conduit 70 and then released from the housing in the air passageway. Once deployed, the obstruction device precludes inhaled air from entering the lung portion to be collapsed. It is preferable that the obstruction device take the form of a one-way valve. In addition to precluding inhaled air from entering the lung portion, the device further allows air within the lung portion to be exhaled. This results in more rapid collapse of the lung portion. However, obstruction devices which preclude both inhaled and exhaled air flow may be deployed by the system and method of the invention.

Figure 3:
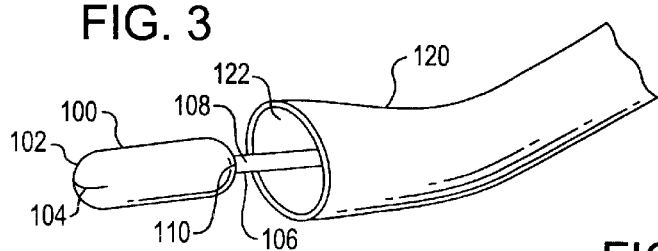
FIG. 3 is a perspective view, illustrating a housing for the bronchial obstruction device and a conduit embodying the present invention.
Figure 4:
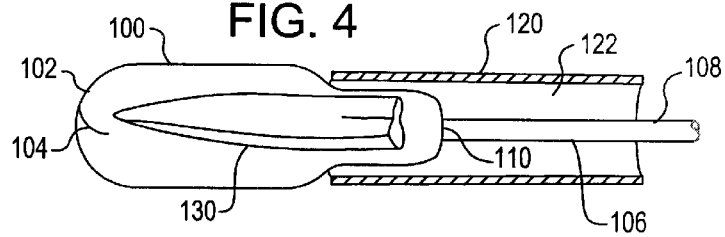
FIG. 4 is a partial cross-sectional view of the housing exiting the distal end of the conduit.

FIGS. 3 and 4 show a bronchial obstruction device housing 100 and a conduit 120 embodying the present invention. The housing 100 forms a sealed capsule structure for housing a bronchial obstruction device 130 to be deployed within an air passageway. The housing 100 has a rounded distal end 102. The rounded configuration of the distal end 102 assists in the guiding of the housing to a desired location within the air passageway. The housing 100, as best seen in FIG. 4 is formed of a flexible, biocompatible material for collapsing within the internal lumen 122 of the conduit 120 as it is advanced through the conduit.

The housing distal end 102 further includes a score or notch 104 to enable the distal end 104 of the housing 100 to be broken-away during deployment of the device 130 without breaking the seal within the housing 100 until the time of deployment.

The housing still further includes a tubular extension 106 having an internal lumen 108. The lumen 108 communicates with the interior of the housing 100 during deployment of the device 130 but may be separated therefrom by a breakable wall 110. As will be seen subsequently, the breakable wall 110 maintains the seal of the housing while permitting a pusher to be advanced through the lumen 108 to break through the wall 110 at the time of deployment to then engage the device 130. With the device 130 thus engaged, further distal advancement of the pusher causes the device to break through the distal end 102 of the housing weakened by the notch 104. Still further advancement of the pusher then releases the device 130 from the housing 100 for deployment of the device 130 at the desired location within the air passageway.

Hence, the device 130 may be deployed in a controlled manner. Further, the seal of the housing 100 is not broken until the time of deployment, rendering the process sterile.

Figure 5:
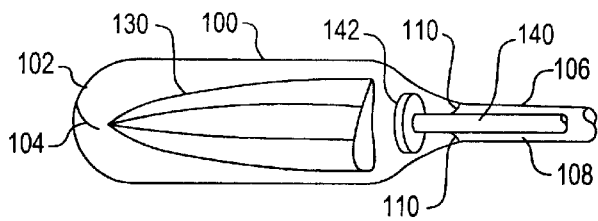
FIG. 5 is a side view illustrating a pusher just prior to engaging the bronchial obstruction device.
Figure 6:
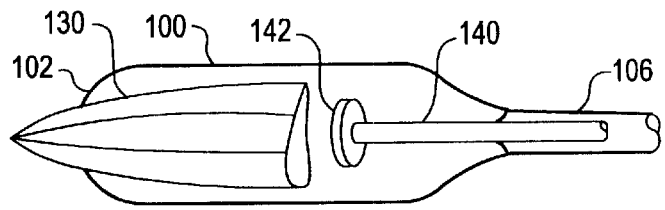
FIG. 6 is another side view illustrating the device being released from the housing by the pusher.
Figure 7:
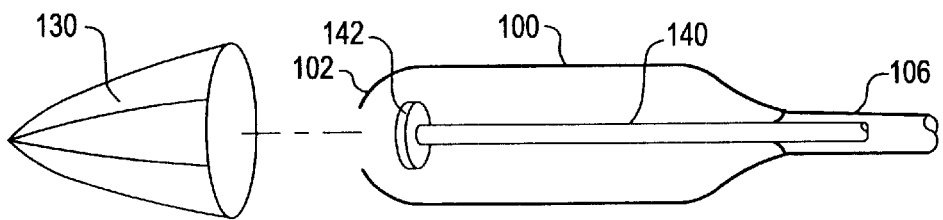
FIG. 7 is another side view of the device, the housing, and the pusher immediately after the device is released from the housing.

FIGS. 5–7 better illustrate the foregoing process. In FIG. 5 it may be seen that the pusher 140 has been advanced through the lumen 108 of the extension 106 and has broken through the wall 110 previously separating the housing 100 from the lumen 108. In accordance with this embodiment, the pusher includes a disc shaped end 142 for engaging the device 130. Alternatively, the pusher 140 may be an appropriately shaped wire or rod. The end 142 may have a diameter dimension slightly less than the diameter dimension of the lumen 108. Alternatively, the extension 106 may be formed of material flexible enough to permit the end 142 to be slightly greater than the diameter of the lumen 108. This allows the extension 106 to be slightly deformed as the end 142 of the pusher 140 is advanced down the extension. In either arrangement, the pusher is slidable down the extension to break through the wall 110 and enter the housing 100.

As seen in FIG. 6. once the pusher end 142 is within the housing 100, it then engages the device 130 upon further distal advancement. The pusher 140 then pushes the device 130 distally to break through the break-away distal end 102 of the housing 100.

Further advancement of the pusher 140 causes the device 130 to be released from the housing. Once released, the device 130 is permitted to expand for deployment. Such a device is shown and described in the aforementioned U.S. Pat. No. 6,258,100. As previously mentioned, other forms of bronchial obstruction devices may be deployed with the present invention. Such devices may be one-way valves, totally blocking, expandable, or non-expandable.

Figure 8:
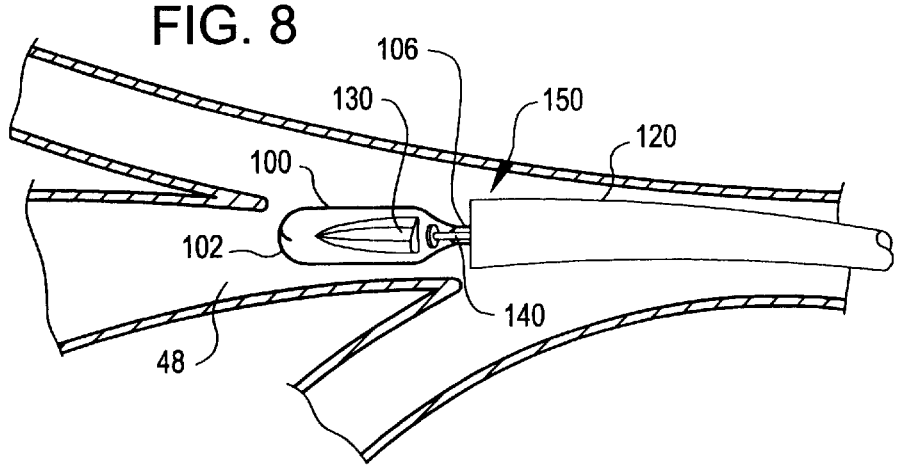
FIG. 8 is a side view illustrating an intermediate step in deploying a bronchial obstruction device in accordance with an embodiment of the present invention.
Figure 9:
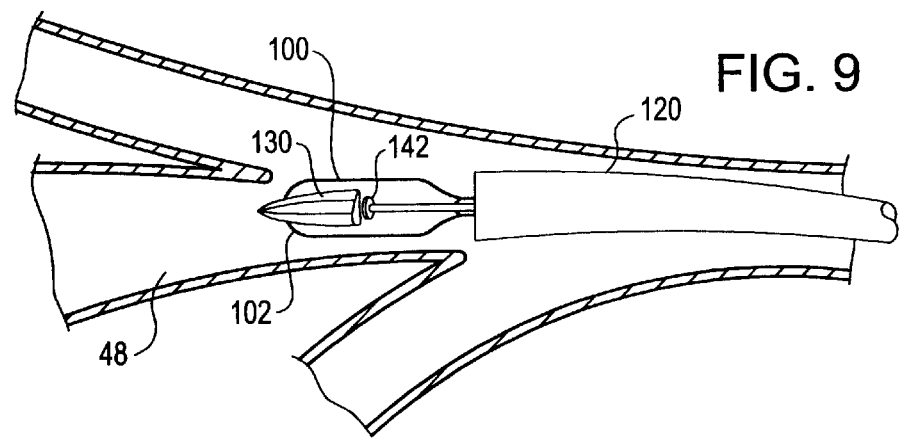
FIG. 9 is another side view illustrating a further step in the deployment of the device.
Figure 10:
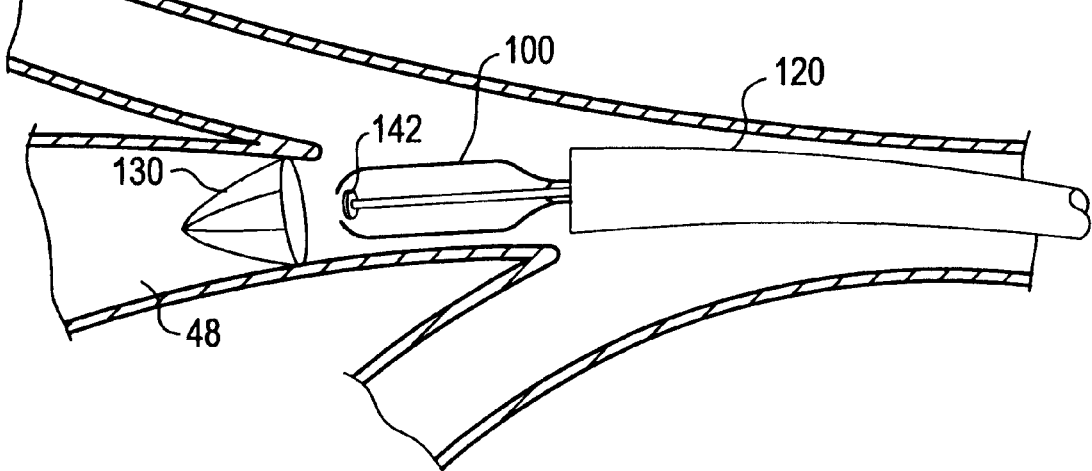
FIG. 10 is a side view illustrating the device after deployment.

FIGS. 8–10 show a complete system 150 embodying the present invention deploying the device 130 within an air passageway, such as bronchial branch sub-branch 48. The system 150 generally includes the conduit 120, the housing 100, the housing extension 106, and the pusher 140 as previously described. In FIG. 8 it may be seen that the conduit 120 has been advanced such that its distal end is just proximal to the bronchial sub-branch 48. The housing 100 has also been advanced through the conduit so that its distal end 102 is within the bronchial sub-branch 48. The pusher has also been advanced into the housing 100 for engagement with the device 130.

As seen in FIG. 9, the pusher end 142 is within the housing 100. It then engages the device 130 and upon further distal advancement, the pusher 140 pushes the device 130 distally to break through the break-away distal end 102 of the housing 100.

Further advancement of the pusher 140 causes the device 130 to be released from the housing in the bronchial sub-branch 48. Once released, the device 130 is permitted to expand for deployment in the bronchial sub-branch 48. Again, the device 130 may be of the type shown and described in the aforementioned U.S. Pat. No. 6,258,100. The now expanded device 130 serves to obstruct the bronchial sub-branch 48 for collapsing the lung portion communicating with the bronchial sub-branch 48.

While particular embodiments of the present invention have been shown and described, modifications may be made, and it is therefore intended in the appended claims to cover all such changes and modifications which fall within the true spirit and scope of the invention.

What is claimed is:

1. A system for deploying a bronchial obstruction device in an air passageway communicating with a lung portion to be at least temporarily collapsed by the bronchial obstruction device, the system comprising:

a conduit configured to be passed down a trachea, into a bronchus communicating with the trachea and into the air passageway communicating with the lung portion, the conduit having an internal lumen; and a capsule dimensioned to house the bronchial obstruction device and to be advanced down the internal lumen into the air passageway, the capsule being configured to release the bronchial obstruction device for deployment in the air passageway.

2. The system of claim 1 wherein the capsule sealingly houses the bronchial obstruction device.

3. The system of claim 2, wherein the sealed chamber maintains sterility of the obstruction device until broken.

4. The system of claim 1 wherein the capsule includes a break-away end portion to release the bronchial obstruction device.

5. The system of claim 1 further including a pusher that pushes the bronchial obstruction device from the capsule.

6. The system of claim 1 further including an elongated extension communicating with the capsule and dimensioned for receiving the pusher.

7. The system of claim 5 further including a break-away wall between the capsule and the elongated extension.

8. The system of claim 1 wherein the capsule is formed of flexible material for collapsing within the internal lumen.

9. The system of claim 1 wherein the capsule is formed of a rigid material.

10. The system of claim 1 wherein the capsule includes a distal end and wherein the distal end of the capsule is configured to release the bronchial obstruction device.

11. The system of claim 10 wherein the distal end of the capsule has a rounded shape.

12. The system of claim 1 wherein the conduit is one of a bronchoscope and a catheter.

13. A system for deploying a bronchial obstruction device in an air passageway communicating with a lung portion to be at least temporarily collapsed by the bronchial obstruction device, the system comprising:

a lumen means for being passed down a trachea, into a bronchus communicating with the trachea and into the air passageway communicating with the lung portion; and deployment means for housing the bronchial obstruction device and dimensioned for advancement down the lumen means into the air passageway, the deployment means having a distal end for releasing the bronchial obstruction device within the air passageway.

14. The system of claim 13 wherein the deployment means sealingly houses the bronchial obstruction device.

15. The system of claim 14, wherein the sealed enclosure means maintains sterility of the obstruction device until broken.

16. The system of claim 13 wherein the distal end of the deployment means includes a break-away portion for releasing the bronchial obstruction device.

17. The system of claim 13 further including pushing means for pushing the bronchial obstruction device from the deployment means.

18. The system of claim 13 wherein the deployment means includes an elongated extension dimensioned for receiving the pushing means.

19. The system of claim 18 further including a break-away wall between the elongated extension and the deployment means.

20. The system of claim 13 wherein the deployment means is formed of flexible material for collapsing within the internal lumen.

21. The system of claim 13 wherein the deployment means is formed of a rigid material.

22. The system of claim 13 wherein the distal end of the deployment means has a rounded shape.

23. The system of claim 13 wherein the lumen means is one of a bronchoscope and a catheter.

24. A method of deploying a bronchial obstruction device in an air passageway communicating with a lung portion to be at least temporarily collapsed, the method including the steps of:

placing the bronchial obstruction device in a housing;

guiding a conduit having an internal lumen down a trachea, into a bronchus communicating with the trachea and into the air passageway communicating with the lung portion;

advancing the housing down the internal lumen of the conduit into the air passageway; and releasing the bronchial obstruction device from the housing to deploy the bronchial obstruction device in the air passageway.

25. The method of claim 24 wherein the placing step includes the step of sealing the bronchial obstruction device in the housing.

26. The method of claim 24 wherein the releasing step includes the step of breaking-away a portion of the housing.

27. The method of claim 24 wherein the releasing step includes the step of pushing the bronchial obstruction device from the housing.

28. A method of deploying a bronchial device in an air passageway, the method including the steps of:

guiding a conduit having an internal lumen down a trachea, into a bronchus communicating with the trachea, and into the air passageway communicating with the lung portion;

advancing a capsule containing the bronchial device down the Internal lumen of the conduit into the air passageway, the capsule having a housing arranged to maintain a sterility of the bronchial device; and releasing the bronchial device from the capsule to deploy the bronchial device in the air passageway.

29. The method of claim 28, wherein the releasing step further includes a step of breaking the housing.

30. An apparatus for deploying a bronchial device in an air passageway, the apparatus comprising:

a breakable capsule arranged to house and to maintain sterility of the bronchial device, the capsule being further arranged to be advanced down an internal lumen of a catheter placed into the air passageway and upon being broken to release the bronchial device for deployment in the air passageway.

31. The apparatus of claim 30, wherein the breakable capsule further includes a sealed chamber for maintaining the sterility of the bronchial device.

32. A system for deploying a bronchial device in an air passageway, the system comprising:

a conduit configured to be passed down a trachea, into a bronchus communicating with the trachea and into the air passageway communicating with the lung portion, the conduit having an internal lumen; and a capsule arranged to house and to maintain a sterility of the bronchial device, and dimensioned to be advanced down the internal lumen into the air passageway, the capsule being further arranged to release the bronchial device for deployment in the air passageway.

33. The system of claim 32, wherein the capsule includes a sealed chamber for maintaining the sterility the bronchial device.

34. The system of claim 32, wherein the capsule includes a break-away end portion for releasing the bronchial device.

* * * * *